US00PP21682P2

(12) United States Plant Patent
Egger

(10) Patent No.: US PP21,682 P2
(45) Date of Patent: Jan. 25, 2011

(54) *HEUCHERA* PLANT NAMED 'MILAN'
(50) Latin Name: ***Heuchera* hybrid**
Varietal Denomination: Milan

(75) Inventor: Janet N. Egger, Wilsonville, OR (US)
(73) Assignee: Terra Nova Nurseries, Inc., Canby, OR (US)

( * ) Notice: Subject to any disclaimer, the term of this patent is extended or adjusted under 35 U.S.C. 154(b) by 0 days.

(21) Appl. No.: 12/658,174

(22) Filed: Feb. 3, 2010

(51) Int. Cl.
*A01H 5/00* (2006.01)

(52) U.S. Cl. ..... Plt./440
(58) Field of Classification Search ..... Plt./440

See application file for complete search history.

*Primary Examiner*—Kent L Bell
(74) *Attorney, Agent, or Firm*—Klarquist Sparkman, LLP

(57) ABSTRACT

A new and distinct hybrid of *Heuchera* plant characterized by being very free flowering on short flower stalks, having a very long bloom time (bloom from early spring to late fall in Canby, Oreg.), excellent flower size and color, a well branched, mounding habit, and excellent vigor.

1 Drawing Sheet

Botanical denomination: *Heuchera* hybrid.
Variety designation: 'Milan'.
Cross Reference to *Heuchera* 'Shanghai' (U.S. Plant patent application Ser. No. 12/653,617).

BACKGROUND OF THE INVENTION

The present invention relates to a new and distinct cultivar of *Heuchera* and given the cultivar name of 'Milan'. *Heuchera* is in the family Saxifragaceae. *Heuchera* 'Milan' originated from a cross between *Heuchera* 766-5, a proprietary non-commercial hybrid, as the seed parent, and *Heuchera* 758-1, a proprietary non-commercial hybrid, as, as the pollen parent.

Compared to the seed parent, *Heuchera* 766-5, the new cultivar has smaller leaf size, warm purplish pink rather than light pink to white flowers, silver rather than purple leaves.

Compared to the pollen parent, *Heuchera* 758-1, the new cultivar has larger, darker pink flowers, bigger leaves with more purple tones on the new growth.

Compared to *Heuchera* 'Paris' (U.S. Plant Pat. No. 18,881), the new cultivar has smaller leaves that are purple to silver rather than veiled green leaves.

Compared to *Heuchera* 'Shanghai' (U.S. Plant patent application Ser. No. 12/653,617), the new cultivar has lighter colored leaves and pink rather than ivory flowers.

This new *Heuchera* is uniquely distinguished by:

1. very free flowering on short flower stalks,
2. very long bloom time (bloom from early spring to late fall in Canby, Oreg.),
3. excellent flower size and color,
4. well branched, small, mounding habit,
5. excellent vigor.

This new cultivar has been reproduced only by asexual propagation (tip cuttings and tissue culture). Each of the progeny exhibits identical characteristics to the original plant. Asexual propagation by division and tissue culture using standard micropropagation techniques with terminal and lateral shoots, as done in Canby, Oreg., shows that the foregoing characteristics and distinctions come true to form and are established and transmitted through succeeding propagations. The present invention has not been evaluated under all possible environmental conditions. The phenotype may change with variations in environment without a change in the genotype of the plant.

BRIEF DESCRIPTION OF THE DRAWING

The photo shows a 10-month-old plant of *Heuchera* 'Milan' growing in the ground in full sun in the garden in August in Canby, Oreg.

DETAILED PLANT DESCRIPTION

The following is a detailed description of the new *Heuchera* cultivar based on observations taken in November of eleven-month-old specimens growing in the ground in the trial bed in full sun and with added irrigation in the summer months in Canby, Oreg. Canby is Zone 8 on the USDA Hardiness map. Temperatures range from a high of 95 degrees F. in August to and average of 32 degrees F. in January. Normal rainfall in Canby is 42.8 inches per year. The color descriptions are all based on The Royal Horticultural Society Colour Chart.

Plant:

*Form.*—Basal rosette, herbaceous perennial.
*Hardiness.*—USDA Zone 4 to 9.
*Size.*—23 cm tall from top of the foliage to the ground and 39 cm wide.
*Habit.*—Mounding, with high crown number.
*Vigor.*—Excellent.

Leaf:

*Type.*—Simple.
*Arrangement.*—Rosette.
*Shape.*—Broadly ovate.
*Lobing/division.*—5 lobes, the terminal is the longest; shallow secondary lobes.
*Venation.*—Palmate.
*Margins.*—Broadly crenate and somewhat undulate.
*Apex.*—Mucronulate.

*Base.*—Cordate, lobes overlapping at the base.
*Blade size.*—Grows to 7.5 cm long and 7.3 cm wide.
*Texture.*—Leathery.
*Surface texture.*—Glabrous on the top and glandular on the bottom.
*Petiole description.*—Grows to 12 cm long and 2 mm wide, glandular hairs, closest to Greyed Orange 177A.
*Leaf color.*—Topside, spring leaves are silver purple with dark veins, Black 202C tinted Purple 77A with veins Black 202A; mature summer thru winter leaves are closest to Grey 201B with the veins closest to Black 202A, young summer to fall leaves are closest to Grey 201B with a overall tint of Red Purple 59A with the veins closest to Black 202A; bottom side spring closest to Greyed Purple 187A, summer to winter Red Purple 59A.

Inflorescence:
*Size.*—Grows to 8.5 cm wide and 18 cm long.
*Type.*—Thyrse.
*Number of flowers per thyrse.*—About 75.
*Number of thyrse.*—About 40 for the whole flowering season.
*Peduncle.*—About 42 cm long, 3 mm wide at base, Greyed Purple 187A, glandular hairs, with no cauline leaves.
*Pedicel.*—Variable in size, with glandular hairs, Greyed Purple 187A.
*Bloom period.*—May through November in Canby, Oreg.

Flower bud:
*Size.*—4 mm wide and 5.5 mm long.
*Description.*—Glandular puberulent, ovoid, downfacing.
*Color.*—Red Purple 63A.

Flower:
*Type.*—Perfect.
*Shape.*—Campanulate.
*Size.*—8 mm long and 7 mm wide.
*Corolla description.*—5 in number, 3 mm long and 2 mm wide, broadly spatulate, sometimes once lobed, tip acute, margin entire, glandular on both sides, Red Purple 62A.
*Calyx description.*—Campanulate, 8 mm long and 7 mm wide, with 5 lobes divided ½ way to the base, each 3 mm wide and 4 mm long, glandular hairs outside and inside, tips obtuse, margin entire; inside color on bottom half Red Purple 63D and top half Red Purple 63B, outside color base and tips are Red Purple 63A and middle Red Purple 63B.
*Stamen description.*—5 in number, filaments 2 mm long, Red Purple 62D, anthers sterile, 0.5 mm, Yellow Orange 23A.
*Pistil description.*—1, 2-beaked, 3 mm long; ovary 1 mm long, Yellow 12D; style 2 mm long, Yellow 12D, stigma Yellow Orange 18A.
*Fragrance.*—None.
*Lastingness.*—Each thyrse blooms for about 3 weeks on the plant.

Fruit: None produced.
Seed: None.
Pest and disease tolerance: Excellent disease resistance to powdery mildew, the common problem of *Heuchera*. Susceptible to *Heuchera* rust and root weevils.

I claim:
1. A new and distinct *Heuchera* plant as herein illustrated and described.

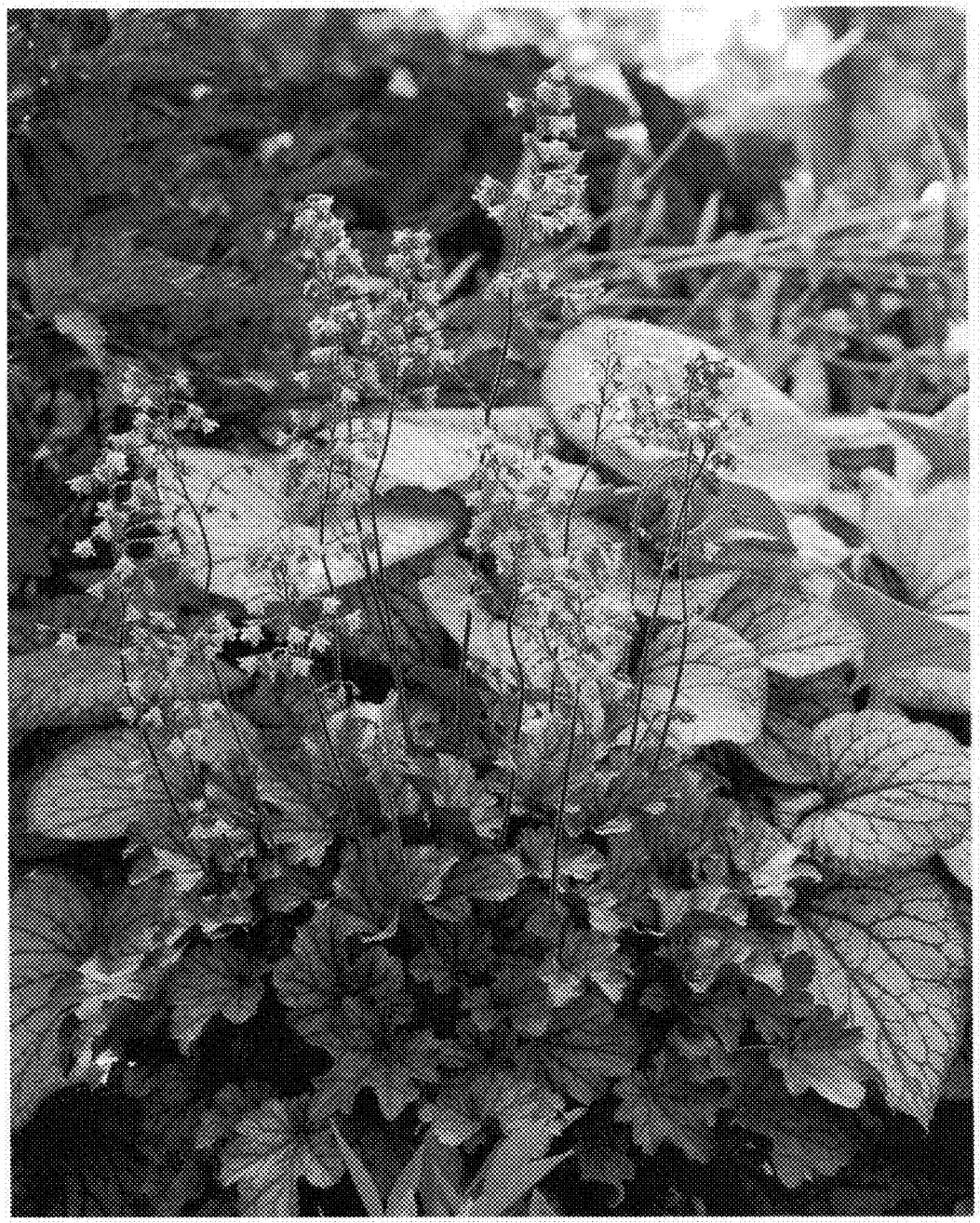

* * * * *